United States Patent

Brooks et al.

[11] Patent Number: 5,288,751
[45] Date of Patent: Feb. 22, 1994

[54] [(SUBSTITUTED) PHENYALKYL]FURYLALKYNYL-AND [SUBSTITUTED) PHENYALKYL] THIENYLALKYNYL-N-HYDROXYUREA INHIBITORS OR LEUKOTRIENE BIOSYNTHESIS

[75] Inventors: Dee W. Brooks, Libertyville; Andrew O. Stewart, Wildwood; Anwer Basha, Lake Forest; Pramila Bhatia, Mundelein; James D. Ratajczyk, Waukegan, all of Ill.

[73] Assignee: Abbott Laboratories, Abbott Park, Ill.

[21] Appl. No.: 973,100

[22] Filed: Nov. 6, 1992

[51] Int. Cl.$^5$ .................. C07D 307/36; C07D 333/22; A61K 31/34; A61K 31/38
[52] U.S. Cl. .................................................... 514/438
[58] Field of Search ............... 549/62, 77, 475, 491; 514/438, 446, 471, 473

[56] References Cited

FOREIGN PATENT DOCUMENTS

WO92/01682 2/1992 PCT Int'l Appl. ........ C07D 333/36
WO92/10469 6/1992 PCT Int'l Appl. ........ C07D 275/64

*Primary Examiner*—Alan L. Rotman
*Attorney, Agent, or Firm*—Jerry F. Janssen

[57] ABSTRACT

The present invention relates to compounds of the formula

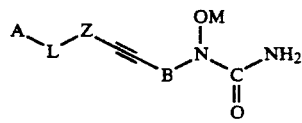

and the pharmaceutically acceptable salts thereof wherein Z is selected from optionally substituted phenyl, furyl, thienyl or thiazolyl; which inhibits leukotriene biosynthesis and is useful in the treatment of inflammatory disease states; also disclosed are leukotriene biosynthesis inhibiting compositions and a method for inhibiting 5-lipoxygenase activity and leukotriene biosynthesis.

10 Claims, No Drawings

[(SUBSTITUTED) PHENYALKYL]FURYLALKYNYL-AND [SUBSTITUTED) PHENYALKYL] THIENYLALKYNYL-N-HYDROXYUREA INHIBITORS OR LEUKOTRIENE BIOSYNTHESIS

TECHNICAL FIELD

This invention relates to compounds having activity to inhibit lipoxygenase enzyme activity, to pharmaceutical compositions comprising these compounds, and to a medical method of treatment. More particularly, this invention concerns certain substituted arylalkynyl- and ((heteroaryl)alkynyl)-N-hydroxyureas which inhibit leukotriene biosynthesis, to pharmaceutical compositions comprising these compounds and to a method of inhibiting leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 299 761 to Salmon, et al. discloses and claims certain (substituted phenoxy)-phenylalkenyl hydroxyamic acids and their salts which are useful as agents for inhibiting lipoxygenase and cyclooxygenase activity.

European Patent Application (Case number 4824) to Brooks, et al. discloses and claims certain substituted alkynyl ureas and hydroxamic acid, which do not contain spacer groups, having lipoxygenase inhibiting activity.

SUMMARY OF THE INVENTION

In its principal embodiment, the present invention provides certain N-[((substituted)aryl)alkynyl]- and N-[((substituted)heteroaryl)alkynyl]-N-hydroxyurea compounds which inhibit 5-lipoxygenase enzyme activity and thus leukotriene biosynthesis and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The present invention provides a compound of the structure

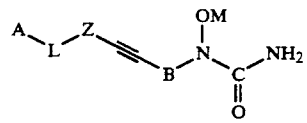

or a pharmaceutically acceptable salt thereof where

M represents hydrogen, a pharmaceutically acceptable cation, or a pharmaceutically acceptable metabolically cleavable group.

B is a straight or branched divalent alkylene group of from one to twelve carbon atoms.

Z is selected from the group consisting of (a) phenyl, optionally substituted with alkyl of from one to six carbon atoms, haloalkyl of from one to six carbon atoms, alkoxy of from one to twelve carbon atoms, or halogen; b) furyl, optionally substituted with alkyl of from one to six carbon atoms, or haloalkyl of from one to six carbon atoms; (c) thienyl, optionally substituted with alkyl of from one to six carbon atoms, or haloalkyl of from one to six carbon atoms; (d) thiazolyl, optionally substituted with alkyl of from one to six carbon atoms or haloalkyl of from one to six carbon atoms.; and (e) oxazolyl, optionally substituted with alkyl of from one to six carbon atoms or haloalkyl of from one to six carbon atoms.

L selected from the group consisting of (a) alkylene of from 1–6 carbon atoms, (b) alkenylene of from 1–6 carbon atoms, (c) alkynylene of from 1–6 carbon atoms, (d) >C=O, (e) >C=N—OR$_1$, wherein R$_1$ is hydrogen or C$_1$–C$_6$ alkyl, (f) —(CHR$_1$)$_n$(CO)(CHR$_2$)$_m$, where n and m are independently selected from an integer from one to six and R$_1$ and R$_2$ are independently selected from hydrogen or $C_1-C_6$-alkyl, (g) $-(CHR_1)_nC=NOR_2$, where $R_1$, $R_2$ and n are as defined above; (h) $-(CHR_1)_nON=CR_2$, where $R_1$, $R_2$ and n are as defined above; (i) $-(CHR_1)_n-O-(CHR_2)_m-$, where $R_1$, $R_2$, n and m are as defined above, (j) $-(CHR_1)_n-NR_2(CHR_3)_m-$, where $R_1$, $R_2$, n and m are as defined above and $R_3$ is selected from hydrogen or $C_1-C_6$-alkyl; k) $-(CHR_1)_n-S-(CHR_2)_m-$, where $R_1$, $R_2$, n and m are as defined above; and (l) $-(CHR_1)_n-(SO_2)-(CHR_2)_m-$, where $R_1$, $R_2$, n and m are as defined above.

A is selected from the group consisting of (a) carbocyclic aryl optionally substituted with (a-1) alkyl of from one to six carbon atoms, (a-2) haloalkyl of from one to six carbon atoms, (a-3) hydroxyalkyl of from one to six carbon atoms, (a-4) alkoxy of from one to twelve carbon atoms, (a-5) alkoxyalkoxyl in which the two alkoxy portions may each independently contain from one to six carbon atoms, (a-6) alkylthio of from one to six carbon atoms, (a-7) hydroxy, (a-8) halogen, (a-9) cyano, (a-10) amino, (a-11) alkylamino of from one to six carbon atoms, (a-12) dialkylamino in which the two alkyl groups may independently contain from one to six carbon atoms, (a-13) alkanoylamino of from two to eight carbon atoms, (a-14) N-alkanoyl-N-alkylamino in which the alkanoyl may contain from two to eight carbon atoms and the alkyl groups may contain from one to six carbon atoms, (a-15) alkylaminocarbonyl of from two to eight carbon atoms, (a-16) dialkylaminocarbonyl in which the two alkyl groups may independently contain from one to six carbon atoms, (a-17) carboxyl, (a-18) alkoxycarbonyl of from two to eight carbon atoms, (a-19) phenyl, optionally substituted with (a-19-a) alkyl of from one to six carbon atoms, (a-19-b) haloalkyl of from one to six carbon atoms, (a-19-c) alkoxy of from one to six carbon atoms, (a-19-d) hydroxy or (a-19-e) halogen; (a-20) phenoxy, optionally substituted with (a-20-a) alkyl of from one to six carbon atoms, (a-20-b) haloalkyl of from one to six carbon atoms, (a-20-c) alkoxy of from one to six carbon atoms, (a-20-d) hydroxy or (a-20-e) halogen; (a-21) phenylthio, optionally substituted with (a-21-a) alkyl of from one to six carbon atoms, (a-21-b) haloalkyl of from one to six carbon atoms, (a-21-c) alkoxy of from one to six carbon atoms, (a-21-d) hydroxy or (a-21-e) halogen; (a-22) pyridyl, optionally substituted with (a-22-a) alkyl of from one to six carbon atoms, (a-22-b) haloalkyl of from one to six carbon atoms, (a-22-c) alkoxy of from one to six carbon atoms, (a-22-d) hydroxy or (a-22-e) halogen; (a-23) pyridyloxy, optionally substituted with (a-23-a) alkyl of from one to six carbon atoms, (a-23-b) haloalkyl of from one to six carbon atoms, (a-23-c) alkoxy of from one to six carbon atoms, (a-23-d) hydroxy or (a-23-e) halogen; (b) furyl, optionally substituted with (b-1) alkyl of from one to six carbon atoms, (b-2) haloalkyl of from one to six carbon atoms, (b-3) halogen, (b-4) phenyl, optionally substituted with (b-4-a) alkyl of from one to six carbon atoms, (b-4-b) haloalkyl of from one to six carbon atoms, (b-4-c) alkoxy of from one to six carbon atoms, (b-4-d) hydroxy or (b-4-e) halogen; (b5) phenoxy, optionally substituted with (b-5-a) alkyl of from one to six carbon atoms, (b-5-b) haloalkyl of from one to six carbon atoms, (b-5-c) alkoxy of from one to six carbon atoms, (b-5-d) hydroxy or (b-5-e) halogen, (b-6) phenylthio, optionally substituted with (b-6-a) alkyl of from one to six carbon atoms, (b-6-b) haloalkyl of from one to six carbon atoms, (b-6-c) alkoxy of from one to six carbon atoms, (b-6-d) hydroxy or (b-6-e) halogen, (b-7) pyridyl, optionally substituted with (b-7-a) alkyl of from one to six carbon atoms, (b-7-b) haloalkyl of from one to six carbon atoms, (b-7-c) alkoxy of from one to six carbon atoms, (b-7-d) hydroxy or (b-7-e) halogen, (b-8) pyridyloxy, optionally substituted with (b-8-a) alkyl of from one to six carbon atoms, (b-8-b) haloalkyl of from one to six carbon atoms, (b-8-c) alkoxy of from one to six carbon atoms, (b-8-d) hydroxy or (b-8-e) halogen; (c) benzo[b]furyl, optionally substituted with (c-1) alkyl of from one to six carbon atoms; (c-2) haloalkyl of from one to six carbon atoms; (c-3) alkoxyl of from one to six carbon atoms; (c-4) hydroxy; or (c-5) halogen; (d) thienyl, optionally substituted with (d-1) alkyl of from one to six carbon atoms; (d-2) phenyl, optionally substituted with (d-2-a) alkyl of from one to six carbon atoms, (d-2-b) haloalkyl of from one to six carbon atoms, (d-2-c) alkoxy of from one to six carbon atoms, (d-2-d) hydroxy, or (d-2-e) halogen, (d-3) phenoxy, optionally substituted with (d-3-a) alkyl of from one to six carbon atoms, (d-3-b) haloalkyl of from one to six carbon atoms, (d-3-c) alkoxy of from one to six carbon atoms, (d-3-d) hydroxy or (d-3-e) halogen, (d-4) phenylthio, optionally substituted with (d-4-a) alkyl of from one to six carbon atoms, (d-4-b) haloalkyl of from one to six carbon atoms, (d-4-c) alkoxy of from one to six carbon atoms, (d-4-d) hydroxy or (d-4-e) halogen; (d-5) pyridyl, optionally substituted with (d-5-a) alkyl of from one to six carbon atoms, (d-5-b) haloalkyl of from one to six carbon atoms, (d-5-c) alkoxy of from one to six carbon atoms, (d-5-d) hydroxy or (d-5-e) halogen; (d-6) pyridyloxy, optionally substituted with (d-6-a) alkyl of from one to six carbon atoms, (d-6-b) haloalkyl of from one to six carbon atoms, (d-6-c) alkoxy of from one to six carbon atoms, (d-6-d) hydroxy or (d-6-e) halogen; (e) benzo[b]thienyl, optionally substituted with (e-1) alkyl of from one to six carbon atoms; (e-2) haloalkyl of from one to six carbon atoms; (e-3) alkoxyl of from one to six carbon atoms; (e-4) hydroxy, or (e-5) halogen; (f) pyridyl, optionally substituted with (f-1) alkyl of from one to six carbon atoms, (f-2) haloalkyl of from one to six carbon atoms; (f-3) alkoxyl of from one to six carbon atoms; (f-4) hydroxy, or (f-5) halogen; (g) quinolyl, optionally substituted with (g-1) alkyl of from one to six carbon atoms; (g-2) haloalkyl of from one to six carbon atoms; (g-3) alkoxyl of from one to six carbon atoms; (g-4) hydroxy, or (g-5) halogen; and (h) indolyl, optionally substituted with (h-1) alkyl of from one to six carbon atoms; (h-2) haloalkyl of from one to six carbon atoms; (h-3) alkoxyl of from one to six carbon atoms; (h-4) hydroxy, or (h-5) halogen.

In another embodiment, the present invention also provides pharmaceutical compositions which comprise a therapeutically effective amount of compound of as defined above in combination with a pharmaceutically acceptable carrier.

In yet another embodiment, the present invention provides a method of inhibiting lipoxygenase enzyme activity and thereby leukotirene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure -NHR' wherein R' is alkyl, as previously defined, Examples of alkylamino include methylamino, ethylamino, iso-propylamino and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, iso-propylaminocarbonyl and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The term "alkanoylamino" refers to an alkanoyl group, as previously defined, attached to the parent molecular moiety through a nitrogen atom. Examples of alkanoylamino include formamido, acetamido, and the like.

The term "N-alkanoyl-N-alkylamino" referes to an alkanoyl group, as previously defined, attached to the parent molecular moiety through an aminoalkyl group. Examples of N-alkanoyl-N-alkylamino include N-methylformamido, N-methyl-acetamido, and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkoxyl" refers to an alkyl group, as defined above, attached through an oxygen to an alkyl group, as defined above, attached in turn through an oxygen to the parent molecular moiety. Examples of alkoxyalkoxyl include methoxymethoxyl, methoxyethyoxyl, ethoxyethoxyl and the like.

The term "alkoxyalkyl" refers to an alkoxy group, as defined above, attached through an alkylene group to the parent molecular moiety.

The term "alkoxycarbonyl" represents an ester group; i.e. an alkoxy group, attached to the parent molecular moiety through a carbonyl group such as methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynylene" refers to a divalent group derived by the removal of two hydrogen atoms from a straight or branched chain acyclic hydrocarbon group containing a carbon-carbon triple bond. Examples of alkynylene include —C≡CH—, —C≡C—CH$_2$—, —C≡C—CH(CH$_3$)—, and the like.

The term "carbocyclic aryl" denotes a monovalent carbocyclic ring group derived by the removal of a single hydrogen atom from a monocyclic or bicyclic fused or non-fused ring system obeying the "4n+2 p electron" or Huckel aromaticity rule. Examples of carbocyclic aryl groups include phenyl, 1- and 2-naphthyl, biphenylyl, fluorenyl, and the like.

The term "(carbocyclic aryl)alkyl" refers to a carbocyclic aryl ring group as defined above, attached to the parent molecular moiety through an alkylene group. Representative (carbocyclic aryl)alkyl groups include phenylmethyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moiety through a sulfur atom and thence through an alklyene group and are typified by phenylthiomethyl, 1- and 2-naphthylthioethyl and the like.

The term "dialkylamino" refers to a group having the structure -NR'R" wherein R' and R" are independently selected from alkyl, as previously defined. Additionally, R' and R" taken together may optionally be —(CH$_2$)$_{kk}$— where kk is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

The term "phenylthio" refers to a phenyl group attached to the parent molecular moiety through a sulfur atom.

The term "pyridyloxy" refers to a pyridyl group attached to the parent molecular moiety through an oxygen atom.

The term "metabolically cleavable group" denotes a group which is cleaved in vivo to yield the parent molecule of the structural formulae indicated above wherein M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$–C$_4$ alkyl, halogen, hydroxy or C$_1$–C$_4$ alkoxy. Specific examples of representative metabolically cleavable groups include acetyl, methoxycarbonyl, benzoyl, methoxymethyl and trimethylsilyl groups.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention may exhibit stereoisomerism by virtue of the presence of one or more asymmetric or chiral centers in the compounds. The present invention contemplates the various stereoisomers and mixtures thereof. Desired enantiomers are obtained by chiral synthesis from commerically available chiral starting materials by methods well known in the art, or may be obtained from mixtures of the enantiomers by resolution using known techniques.

Compounds falling within the scope of the present invention include, but are not limited to:

N-{3-[5-(4-Fluorophenylmethyl)fur-2-yl]-1-methyl-2-propynyl}-N-hydroxyurea;

N-{3-[5-(4-Fluorophenylcarbonyl)fur-2-yl]-1-methyl-2-propynyl}-N-hydroxyurea;

N-Hydroxy-N-{3-[5-(2-phenylethynyl)thien-2-yl]-1-methyl-2-propynyl}urea;

N-Hydroxy-N-{3-[5-(2-[3-pyridyl]ethenyl)fur-2-yl]-1-methyl-2-propynyl}urea;

N-[3-{5-[2-(4-Fluorophenyl]ethenyl)fur-2-yl]-1-methyl-2-propynyl}-N-hydroxyurea;

N-Hydroxy-N-{3-[5-(2-phenylethenyl)fur-2-yl]-1-methyl-2-propynyl}urea;

N-Hydroxy-N-{3-[5-(2-[2-pyridyl]ethenyl)fur-2-yl]-1-methyl-2-propynyl}urea;

N-[3-{5-[2-(4-Fluorophenyl)ethenyl]fur-2-yl}-1-methyl-2-propynyl]-N-hydroxyurea;

N-Hydroxy-N-[3-{5-[2-(5-methylphenyl)ethenyl]fur-2-yl}-1-methyl-2-propynyl]urea;

N-{3-[3-(O-Benzyloxyoximino)phenyl]-1-methyl-2-propynyl}-N-hydroxyurea;

N-Hydroxy-N-{3-[(3-phenylcarbonyl)phenyl]-1-methyl-2-propynyl}urea;

N-{3-[5-(4-Fluorophenylmethyl)-2-thienyl]-1-methyl-2-propynyl}-N-hydroxyurea;

(R)-N-{3-[5-(4-Fluorophenylmethyl)-2-thienyl]-1-methyl-2-propynyl}-N-hydroxyurea;

N-{3-[5-(4-Fluorophenylcarbonyl)-2-thienyl]-1-methyl-2-propynyl}-N-hydroxyurea;

N-{3-[5-(3-Chloropyrid-3-ylmethyl)-2-thienyl]-1-methyl-2-propynyl}-N-hydroxyurea;

(R)-N-{3-[5-(3-Chloropyrid-3-ylmethyl)-2furyl]-1-methyl-2-propynyl}-N-hydroxyurea;

(R)-N-{3-[5-(3-Chloropyrid-3-ylmethyl)-phenyl]-1-methyl-2-propynyl}-N-hydroxyurea;

(R)-N-{3-[5-(4-Chlorophenylmethyl)-2-thienyl]-1-methyl-2-propynyl}-N-hydroxyurea; and (R)-N-{3-[5-(4-Fluorophenylmethyl)-2-thiazolyl]-1-methyl-2-propynyl}-N-hydroxyurea.

Preferred compounds of this invention are those in which Z is optionally substituted thienyl.

A particularly preferred compound is (R)-N-{3-[5-(4-fluorophenylmethyl)-2-thienyl]-1-methyl-2-propynyl}-N-hydroxyurea.

Leukotriene Biosynthesis Inhibition Determination

Inhibition of leukotriene biosynthesis was evaluated in an assay, involving calcium ionophore-induced LTB$_4$ biosynthesis expressed human whole blood. Human heparinized whole blood was preincubated with test compounds or vehicle for 15 min at 37° C. followed by calcium ionophore A23187 challenge (final concentration of 8.3 $\mu$M) and the reaction terminated after 30 minutes by adding two volumes of methanol containing prostaglandin B$_2$ as an internal recovery standard. The methanol extract was analyzed for LTB$_4$ using a commercially available radioimmunoassay.

The compounds of this invention inhibit leukotriene biosynthesis as illustrated in Table 1.

TABLE 1

| In Vitro Inhibitory Potencies Against Stimulated LTB$_4$ Formation in Human Whole Blood | |
|---|---|
| Example | IC$_{50}$ ($\mu$M) or % inhibition |
| 1 | 0.06 |
| 2 | 72% (~0.2) |
| 4 | 39% (~0.8) |
| 5 | 0.62 |
| 6 | 40% (~0.4) |
| 7 | 0.35 |
| 8 | 62% (~0.2) |
| 9 | 0.3 |
| 12 | 0.07 |
| 13 | 0.07 |

INHIBITION OF LEUKOTRIENE BIOSYNTHESIS IN VIVO

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W., *Fed. Proc., Fed. Am. Soc. Exp. Biol.* 1985, 44: 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. Compounds of this invention prevent the formation of leukotrienes in this model after oral administration in a range of 1-200 μmol/kg. Representative activity is demonstrated by Example 1 which provided 68% inhibition of leukotriene and Example 12 which provided 72% inhibition of leukotriene both with a single 30 μmol/kg oral dose.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention can be prepared by a variety of synthetic routes. Representative procedures are outlined as follows.

Scheme 1a illustrates a general route for the preparation of the compounds of this invention involving the assembly of an heteroaryl template that can be functionalized to give the desired acetylenic N-hydroxyurea.

The intermediate 2 (where Y is selected from >O,>S, and —CH=CH—) is prepared by a coupling reaction of the two requisite intermediates shown in Scheme 1a. This reaction may be catalyzed by the addition of transition metal catalysts or their salts. In addition to coupling of metalated aryl intermediates with halide intermediates, other functionalities such as acetylenes and olefins may be coupled under these conditions to give the desired intermediate 2. Alternatively an aryl phosphonate or phosphorane can be reacted with an aldehyde to give intermediate 2. The aryl moiety 2 is then converted to an aryl halide 3 or 4 which is then treated in a Pd catalyzed coupling reaction with an alkynyl-N-hydroxyurea, for example, butynyl-N-hydroxyurea, to provide the desired product 5.

Scheme 1b illustrates an alternative route for the preparation of the compounds of this invention. The intermediate 8 is prepared by coupling the two requisite intermediates 6 and 7 (where M is Li, Na or Mg and Y is O or S). Hydrolysis of the diethylacetal provides the aldehyde 9, which is oxidized to the intermediate carboxylic acid 10 (for example using NaClO$_2$ in DMSO and aqueous NaH$_2$PO$_4$. The carboxylic acid is converted into the iodo compound 11 using NaOH, I$_2$, and KI. Intermediate 11 is then reacted by the procedures described in Scheme 1a with the 1-methyl-2-propynyl-N-hydroxyurea moiety to provide compounds of the general form 5.

Also, the aryl aldehyde 9 (where Y is >O or >S) is converted to the substituted butynol 12 by known methods (for example, treatment with carbon tetrabromide, triphenylphosphine and zinc, followed by lithium diisopropylamide and acetaldehyde). Alternatively aryl halide 11 can be converted to the butynol 12 by Pd catalyzed coupling with 3-hydroxybutyne as shown in Scheme 1c.

Another procedure is shown in Scheme 1d and involved the treatment of the substituted butynol 12 (where Y is >O or >S) with triphenylphosphine, diethyl azodicarboxylate and N,O-bis-phenoxycarbonyl-hydroxylamine followed by treatment with ammonia or ammonium hydroxide to provide the desired N-hydroxyureas 5 of this invention. Alternatively intermediate 11 can be coupled using a suitable palladium catalyst and the 1-methyl-2-propynyl-N-hydroxyurea to give the desired compounds 5 of this invention.

Scheme 1a

-continued
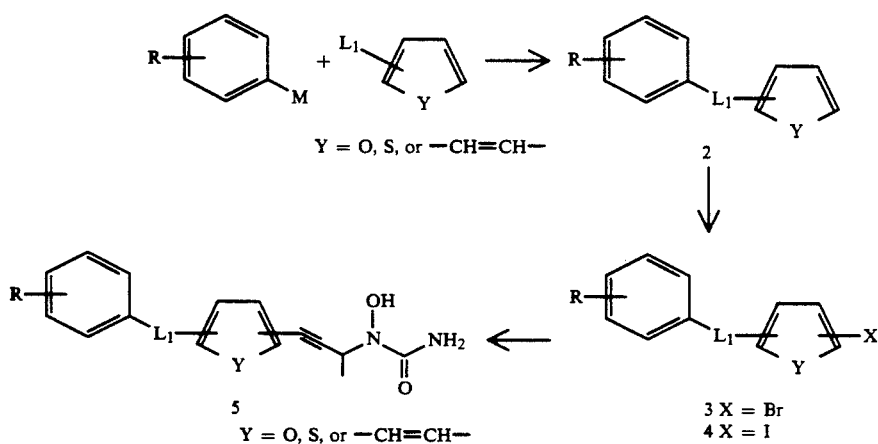
Scheme 1b
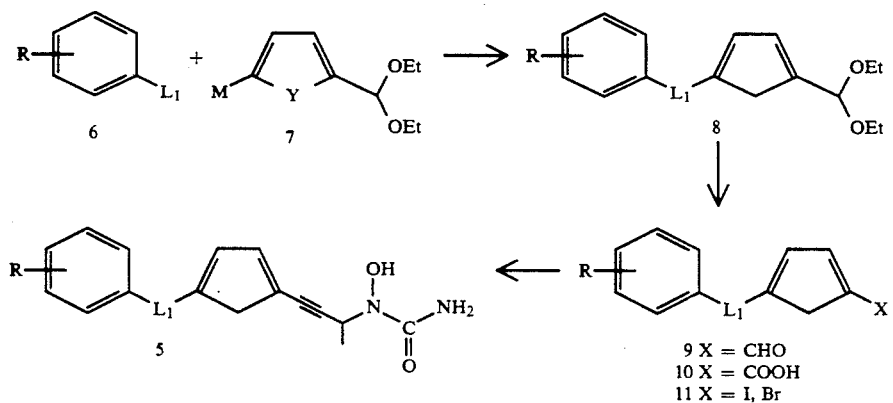
Scheme 1c
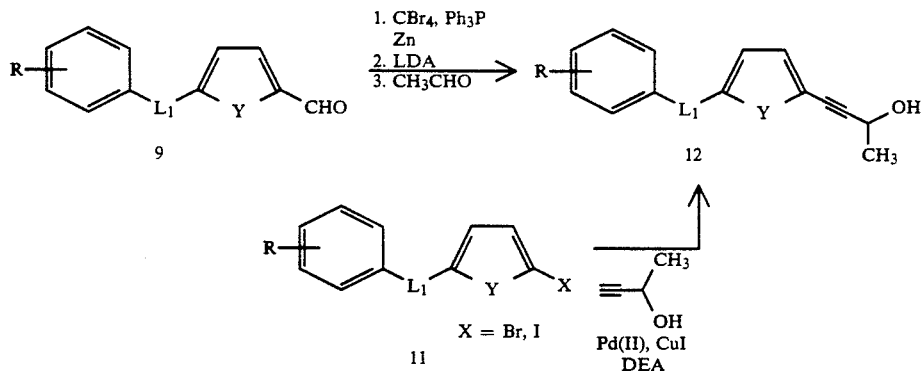
Scheme 1d
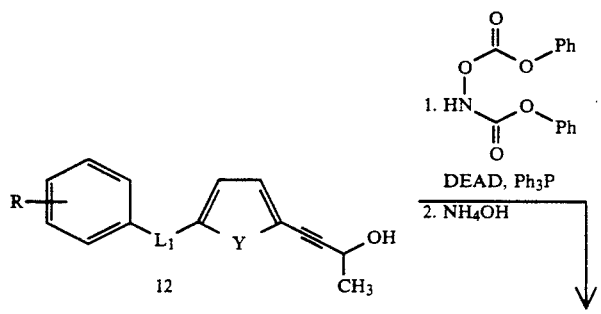

-continued

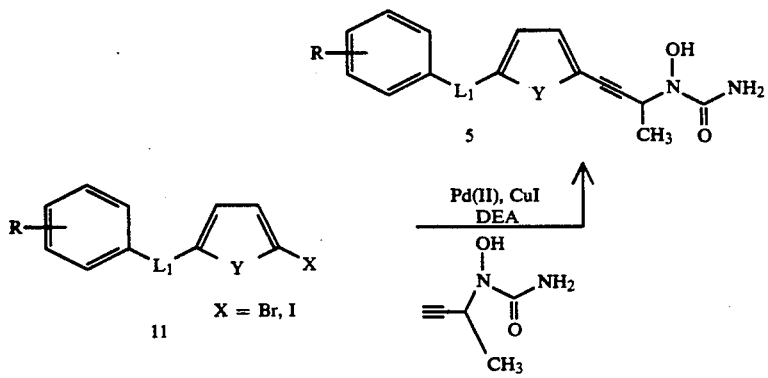

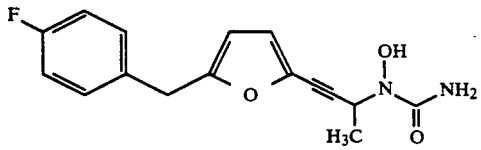

The foregoing may be better understood by reference to the following examples which are provided for illustration and not intended to limit the scope of the inventive concept. The following abbreviations are used: THF for tetrahydrofuran, n-BuLi for n-butyllithium, DMF for N,N-dimethylformamide, CDCl$_3$ for deuterochloroform, DMSO-d$_6$ for deuterodimethylsulfoxide, DIBALH (diisobutylaluminum hydride) for diisobutylaluminum hydride, LAH for lithium aluminum hydride, LDA for lithium diisopropylamide and TDA-1 for tris[2-(2-methoxyethoxy)ethyl]amine.

EXAMPLE 1

N-{3-[5-(4-Fluorophenylmethyl)fur-2-yl]-1-methyl-2-propynyl}-N-hydroxyurea

EXAMPLE 1A 2-(4-Fluorophenylmethyl)furan

To a 0° C. solution of furan (13.6 g, 0.20 mol) in a mixture of anhydrous ether (230 mL) and anhydrous THF (70 mL) under nitrogen was added a 2.5M solution of n-butyllithium in hexane (54.0 mL, 0.134 mol). The mixture was stirred at 0° C. for 1.5 hours and then transferred by cannula to a stirred −78° C. solution of 4-fluorobenzyl bromide (23.6 g, 0.125 mol) and tetrakis(triphenylphosphine)palladium (0) (1.25 g, 0.001 mol) in anhydrous THF (200 mL). The transfer was made under nitrogen over a period of 30–40 minutes. The reaction mixture was stirred at ambient temperature overnight, saturated aqueous solution of ammonium chloride was added and the mixture extracted with ether. The ether layer was dried (MgSO$_4$), concentrated in vacuo and the residue distilled at reduced pressure to give the title compound as a colorless oil (17.89 g, 81%). b.p. 57°–62° C. at 0.5–0.7 mm-Hg.

EXAMPLE 1B

2-Bromo-5-(4-fluorophenylmethyl)furan

To a −30° C. solution of the compound resulting from Example 1A (32.0 g, 0.18 mol) in anhydrous DMF (60 mL) was added a solution of bromine (28.9 g, 0.18 mol) in CH$_2$Cl$_2$ (250 mL). The mixture was stirred for 0.5 hours at −10° C. and poured into pentane (1600 mL). The pentane was then decanted from the dark colored insoluble layer. Evaporation of the pentane gave the crude product which was purified by flash-chromatography on silica gel eluting with pentane to provide the title compound as a cream colored solid in a yield of 8.87 g (19.2%).

EXAMPLE 1C 4-(5-{4-Fluorophenylmethyl}fur-2-yl)-3-butyn-2-ol

A solution of the compound resulting from Example 1B (23.65 g, 92.7 mmol) and D,L-3-butyn-2-ol(8.19 g, 117 mmol) in piperidine (125 mL) was stirred and treated with tetrakis (triphenylphosphine) palladium (0) (0.34 g), copper (I) iodide (0.22 g) and triphenylphosphine (0.22 g). The mixture was stirred under nitrogen and heated to reflux for 1.5 hours, cooled and treated with ice, saturated NH$_4$Cl solution (300 mL) and 3N HCl (300 mL). The mixture was shaken and extracted with CH$_2$Cl$_2$ (2×400 mL). The combined organic layers were washed with additional 3N HCl until the washes were acidic, dried (MgSO$_4$) and concentrated in vacuo. The resulting residue was purified by flash chromatography on silica eluting with CH$_2$Cl$_2$ to afford 17.0 g (75%) of the title compound.

EXAMPLE 1D

N-{3-[5-(4-Fluorophenylmethyl)fur-2-yl]-1-methyl-2-propynyl}-N-hydroxyurea

To a stirred 0° C. solution of the compound resulting from Example 1C (9.37 g, 38.3 mmol), N,O-bis-phenyloxycarbonylhydroxylamine (12.6 g, 46.1 mmol) and triphenylphosphine (13.1 g, 49.9 mmol) in anhydrous THF (800 mL) was added a solution of diisopropyl azodicarboxylate (10.1 g, 49.9 mmol) in anhydrous THF (400 mL) dropwise. The reaction mixture was allowed to warm to ambient temperature, concentrated in vacuo at 45° C. and the residue treated with a 1:1 mixture of ether-pentane (400 mL) and stored overnight at −20° C. The ether-pentane solution was decanted from the solids which had separated and concentrated again in vacuo to a residue which upon purification by flashchromatography on silica gel eluting with 2:1 CH$_2$Cl$_2$-pentane afforded 7.55 g (39%) of N,O-bis phenoxycarbonyl-N-4-(5-{4-fluorophenylmethyl}fur-2-yl)-1-methyl-2-propynyl]hydroxylamine.

A solution of the intermediate prepared above (13.53 g, 27.0 mmol) in methanol (450 mL) was treated with concentrated aqueous ammonium hydroxide (150 mL) and the mixture stirred while stoppered overnight at ambient temperature. The reaction mixture was concentrated in vacuo and the residue purified by flash chromatography on silica eluting with 7% CH₃OH—CH₂Cl₂. The fractions containing the product were combined, concentrated in vacuo and the residue triturated with CH₂Cl₂ to give 4.22 g (52%) of the title compound as a white solid. m.p. 154.5-155.5° C. $^1$H NMR (DMSO-d₆, 300 MHz) δ1.33 (d, J=6 Hz, 3H), 3.96 (s, 2H), 5.12 (q, J=6 Hz, 1H), 6.19 (d, J=3 Hz, 1H), 6.52 (s, 2H), 6.61 (d, J=3 Hz, 1H), 7.10–7.17 (m, 2H), 7.22–7.30 (m, 2H), 9.33 (s, 1H). MS (DCI/NH₃) m/e 303 (M+H)⁺, 320 (M+H+NH₃)⁺. Analysis calcd for C₁₆H₁₅FN₂O₃: C, 63.57; H, 5.00; N, 9.27. Found: C, 63.32; H, 5.01; N, 9.14.

EXAMPLE 2

N-[4-(5-{4-Fluorophenylacetyl}fur-2-yl)-1-methyl-2-propynyl]-N-hydroxyurea

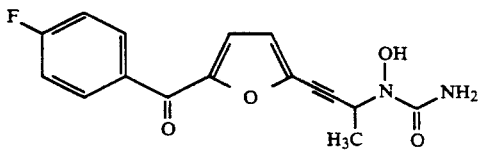

The title compound was prepared according to the procedures described in Example 1 using 4-fluorobenzoyl chloride instead of 4-fluorobenzylbromide in Example 1A, m.p. 154.5°–156° C. $^1$H NMR (DMSO-d₆, 300 MHz) δ1.40 (d, J=6 Hz, 3H), 5.21 (q, J=6 Hz, 1H), 6.60 (s, 2H), 7.01 (d, J=3 Hz, 1H), 7.36–7.46 (m, 3H), 7.95–8.03 (m, 2H), 9.47 (s, 1H). IR (KBR) 3420, 1730, 1595, 1490 cm⁻¹. MS (DCI/NH₃) m/e 317 (M+H)⁺, 334 (M+H+NH₃)⁺. Analysis calcd for C₁₆H₁₃FN₂O₄: C, 60.67; H, 4.14; N, 8.86. Found: C, 60.81; H, 4.08; N, 8.81.

EXAMPLE 3

N-Hydroxy-N-[4-(5-{2-phenylethynyl}thien-2-yl)-1-methyl-2-propynyl]urea

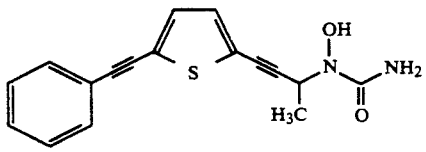

The title compound was prepared according to the procedures described in Example 1 using 2-bromo-5-{2-phenylethynyl}thiophene instead of the substituted bromofuran prepared in step 1B. $^1$H NMR (DMSO-d₆, 300 MHz) δ1.46 (d, J=6 Hz, 3H), 5.17 (q, J=6 Hz, 1H), 6.58 (bs, 2H), 7.25 (d, J=3 Hz, 1H), 7.35 (d, J=3 Hz, 1H), 7.45 (m, 3H), 7.57 (m, 2H), 9.41 (s, 1H). MS (DCI/NH₃) m/e 311 (M+H)⁺, 328 (M+H+NH₃)⁺. Analysis calcd for C₁₇H₁₄N₂O₄S: C, 65.80; H, 4.51; N, 9.03. Found: C, 65.35; H, 4.53; N, 8.92.

EXAMPLE 4

N-Hydroxy-N-[4-(5-{2-[3-pyridyl]ethenyl}fur-2-yl)-1-methyl-2-propynyl]urea

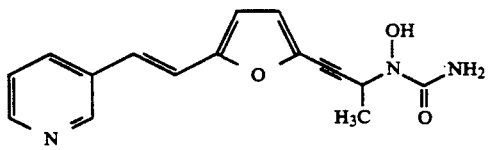

EXAMPLE 4A

2-[2-{3-Pyridyl}ethenyl]furan

To a stirred solution of saturated NaHCO₃ was added 3-picolyl chloride hydrochloride (8.2 g, 50 mmol). After gas evolution ended, the mixture was extracted with CH₂Cl₂. The organic phase was dried (MgSO₄) and concentrated in vacuo. To the resulting residue was added triethylphosphite (8.3 g, 50 mmol) and the neat mixture was stirred and heated to 85° C. overnight. The mixture was cooled and purified by flash column chromotography on silica gel eluting with 5% MeOH—CH₂Cl₂ to afford 3.0 g of diethyl 3-pyridylmethylphosphonate as a yellow oil.

To a stirred −78° C. solution of the above phosphonate (3.0 g, 13 mmol) in THF (50 mL) was added n-butyllithium (25 mL, 55 mmol, 2.5M in hexanes). The cold reaction mixture was stirred 0.5 hours followed by the slow addition of furfuraldehyde (1.24 g, 13 mmol). The reaction was stirred 2 hours at −78° C. and the ice bath removed and allowed to stir at ambient temperature overnight. Saturated NH₄Cl was added and the mixture was diluted with ether. The organic layer was washed with brine, dried (MgSO₄) and concentrated in vacuo. The resuting residue was purified by column chromatography on silica gel eluting with 40% ethyl acetate-hexanes to afford 1.1 g of the title compound.

EXAMPLE 4B

N-Hydroxy-N-[4-(5-{2-[3-pyridyl]ethenyl}fur-2-yl)-1-methyl-2-propynyl]urea

To a stirred −78° C. solution of the compound resulting from Example 4A (0.95 g, 5.5 mmol) in THF (25 mL) was added lithium diisopropylamide (4 mL, 6 mmol, 1.5M in hexanes). The cold reaction mixture was stirred 1 hour, followed by the addition of a THF (3 mL) solution of iodine (1.39 g, 5.5 mmol). The ice bath was removed and the reaction mixture allowed to stir at ambient temperature overnight. Saturated NH₄Cl was added and the mixture diluted with ether. The organic layer was washed with brine, dried (MgSO₄) and concentrated in vacuo. The resulting residue was purified by column chromatography on silica gel eluting with 40% ethyl acetate-hexanes to afford 1.1 g of 2-iodo-5-[2-{3-pyridyl}ethenyl]furan.

To a stirred solution of the above iodofuran (1.4 g, 4.7 mmol) and N-hydroxy-N-(butyn-2-yl)urea (0.64 g, 5 mmol) in diethylamine (10 mL) was added dimethylformamide (1 mL), triphenylphosphine (0.026 g, 0.1 mmol), cuprous iodide (5 mg, 25 μmol) and bis(acetonitrile)palladium(II) chloride (13 mg, 50 μmol). The mixture was stirred overnight at ambient temperature. Aqueous NH₄OH was added and the mixture extracted thoroughly with CH₂Cl₂. The combined organic layer was washed with brine, dried (MgSO₄) and evaporated under reduced pressure. The resulting residue was purified by column chromatography on silica gel eluting with 5% MeOH—CH₂Cl₂ to afford an off-white solid. Recrystallization from ethyl acetate-hexanes gave 530 mg of the title compound. m.p. 166° C. ¹H NMR (DMSO-d₆, 300 MHz) δ1.38 (d, J=7 Hz, 3H), 5.19 (q, J=7 Hz, 1H), 6.61 (bs, 2H), 6.82 (d, J=3 Hz, 1H), 6.82 (d, J=3 Hz, 1H), 7.09 (d, J=16 Hz, 1H), 7.25 (d, J=16 Hz, 1H), 7.39 (m, 1H), 7.77 (m, 1H), 8.03 (m, 1H), 8.45 (m, 1H), 8.77 (m, 1H), 9.43 (s, 1H). MS (DCI/NH₃) m/e 298 (M+H)⁺. Analysis calcd for C₁₆H₁₅N₃O₃: C, 64.63; H, 5.08; N, 14.13. Found: C, 64.01; H, 5.09; N, 14.06.

EXAMPLE 5

N-[4-(5-{2-[4-Fluorophenyl]ethenyl}fur-2-yl)-1-methyl-2-propynyl]-N-hydroxyurea

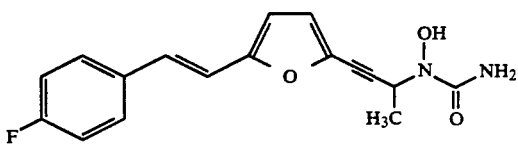

The title compound was prepared following the procedures described in Example 4 using 4-fluorobenzylbromide instead of 3-picolyl chloride hydrochloride. m.p. 177° C. ¹H NMR (DMSO-d₆, 300 MHz) δ1.38 (d, J=7 Hz, 3H), 5.18 (q, J=7 Hz, 1H), 6.56 (d, J=3 Hz, 1H), 6.60 (bs, 2H), 6.80 (d, J=3 Hz, 1H), 7.07 (s, 2H), 7.20 (m, 2H), 7.65 (m, 2H), 9.42 (s, 1H). MS (DCI/NH₃) m/e 315 (M+H)⁺, 332 (M+H+NH₃)⁺. Anal calcd for C₁₇H₁₅FN₂O₃: C, 64.95; H, 4.81; N, 8.91. Found: C, 64.44; H, 4.85; N, 8.85.

EXAMPLE 6

N-Hydroxy-N-[4-(5-{2-phenylethenyl}fur-2-yl)-1-methyl-2-propynyl]urea

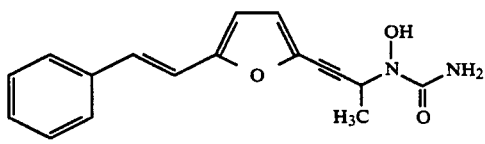

The title compound was prepared following the procedures described in Example 4 using benzylbromide instead of 3-picolyl chloride hydrochloride. m.p. 168° C. ¹H NMR (DMSO-d₆, 300 MHz) δ1.38 (d, J=7 Hz, 3H), 5.19 (q, J=7 Hz, 1H), 6.59 (m, 3H), 6.80 (d, J=3 Hz, 1H), 7.08 (m, 2H), 7.24–7.42 (m, 3H), 7.59 (m, 2H), 9.42 (s, 1H). MS (DCI/NH₃) m/e 297 (M+H)⁺, 314 (M+H+NH₃)⁺. Analysis calcd for C₁₇H₁₆N₂O₃: C, 68.90; H, 5.44; N, 9.45. Found: C, 68.53; H, 5.47; N, 9.42.

EXAMPLE 7

N-Hydroxy-N-[4-(5-{2-[2-pyridyl]ethenyl}fur-2-yl)-1-methyl-2-propynyl]urea

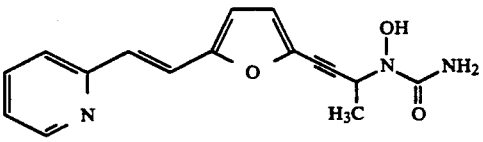

The title compound was prepared following the procedures described in Example 4 using 2-picolyl chloride hydrochloride instead of 3-picolyl chloride hydrochloride. m.p. 175° C. ¹H NMR (DMSO-d₆, 300 MHz) δ1.39 (d, J=7 Hz, 3H), 5.19 (q, J=7 Hz, 1H), 6.61 (bs, 2H), 6.74 (d, J=3 Hz, 1H), 6.82 (d, J=3 Hz, 1H), 7.12 (d, J=16 Hz, 1H), 7.25 (m, 1H), 7.48 (d, J=16 Hz, 1H), 7.54 (d, J=7 Hz, 1H), 7.77 (m, 1H), 8.56 (m, 1H), 9.43 (s, 1H). MS (DCI/NH₃) m/e 298 (M+H)⁺. Analysis calcd for C₁₆H₁₅N₃O₃: C, 64.63; H, 5.08; N, 14.13. Found: C, 64.52; H, 4.84; N, 14.07.

EXAMPLE 8

N-[4-(5-{2-[4-Fluorophenyl]ethenyl}fur-2-yl)-1-methyl-2-propynyl]-N-hydroxyurea

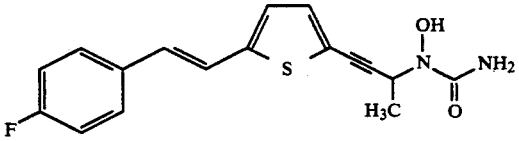

The title compound was prepared following the procedures described in Example 4 using 4-fluorobenzylbromide instead of 3-picolyl chloride hydrochloride and thiophene-2-carboxaldehyde instead of furfuraldehyde. m.p. 177° C. ¹H NMR (DMSO-d₆, 300 MHz) δ1.37 (d, J=7 Hz, 3H), 5.17 (q, J=7 Hz, 1H), 6.58 (bs, 2H), 6.98 (d, J=16 Hz, 1H), 7.10–7.26 (m, 4H), 7.37 (d, J=16 Hz, 1H), 7.63 (m, 2H), 9.39 (s, 1H). MS (DCI/NH₃) m/e 331 (M+H)⁺, 348 (M+H+NH₃)⁺. Analysis calcd for C₁₇H₁₅FN₂O₂S: C, 61.81; H, 4.57; N, 8.48. Found: C, 61.61; H, 4.59; N, 8.47.

EXAMPLE 9

N-Hydroxy-N-[4-(5-{2-[5-methylphenyl]ethenyl}fur-2-yl)-1-methyl-2-propynyl]urea

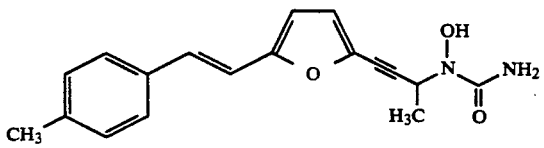

The title compound was prepared following the procedures described in Example 4 using 4-methylbenzylbromide instead of 3-picolyl chloride hydrochloride. m.p. 174° C. ¹H NMR (DMSO-d₆, 300 MHz) δ1.50 (d, J=7 Hz, 3H), 2.33 (s, 3H), 5.26 (q, J=7 Hz, 1H), 6.38 (d, J=3 Hz, 1H), 6.60 (d, J=3 Hz, 1H), 6.87 (d, J=16 Hz, 1H), 7.03 (d, J=16 Hz, 1H), 7.15 (m, 2H), 7.38 (m, 2H). MS (DCI/NH₃) m/e 311 (M+H)⁺, 328

$(M+H+NH_3)^+$. Analysis calcd for $C_{18}H_{18}N_2O_3$: C, 69.65; H, 5.84; N, 9.02. Found: C, 69.50; H, 5.74; N, 8.96.

EXAMPLE 10

N-{4-[3-(O-[Benzyloxycarboxaldoxime)phenyl]-3-butyn-2-y}]-N-hydroxyurea

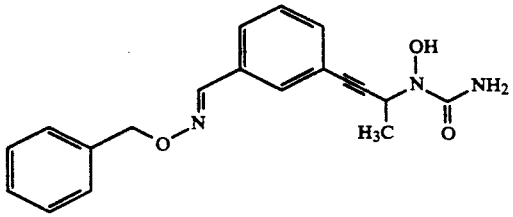

EXAMPLE 10A

N-{4-[3-(Carboxaldehyde diethyl acetal)phenyl]-1-methyl-2-propynyl}-N-hydroxy-urea To a stirred solution of 3-bromobenzaldehyde (22.38 g, 121 mmol) in ethanol (150 mL) was added triethylorthoformate (27 g, 181 mmol) and concentrated HCl (0.5 mL). The mixture was heated to reflux for 3 hours and allowed to cool to ambient temperature. The reaction mixture was poured into ice/H₂O and extracted thoroughly with hexanes. The combined organic extracts were washed with water and brine, dried (MgSO₄) and concentrated in vacuo to give 34 g of 3-bromobenzaldehyde diethyl acetal as a colorless liquid.

To a stirred −78° C. solution of the bromoacetal prepared above (1.0 g, 3.8 mmol) in THF (10 mL) was added n-butyllithium (1.7 mL, 4.25 mmol, 2.5M in hexanes). The cold reaction mixture was stirred 0.5 hours followed by the addition of a THF (5 mL) solution of iodine (1.09 g, 4.25 mmol). The ice bath was removed and the reaction allowed to warm to ambient temperature. Saturated NH₄Cl was added and the mixture diluted with hexanes. The organic layer was washed with brine, dried (MgSO₄) and concentrated under reduced pressure to give a residue which was purified by column chromatography on silica gel eluting with 5% ethyl acetate-hexanes to afford 1.0 g of 3-iodobenzaldehyde diethyl acetal.

To a stirred solution of the iodo acetal (1.0 g, 3.28 mmol) prepared above and N-hydroxy-N-(butyn-2-yl)urea (0.42 g, 3.28 mmol) in diethylamine (5 mL) was added dimethylformamide (0.5 mL), triphenylphosphine (84 mg, 0.32 mmol), cuprous iodide (0.30 mg, 0.16 mmol) and bis(acetonitrile)palladium(II) chloride (115 mg, 0.16 mmol). The mixture was stirred overnight at ambient temperature and aqueous NH₄OH was added. The mixture was extracted thoroughly with ethyl acetate and the combined organic extracts were washed with brine, dried (MgSO₄) and evaporated under reduced pressure. The residue was purified by column chromatography on silica gel eluting with 7% MeOH-Ch₂Cl₂ to afford 0.34 g of the title compound.

EXAMPLE 10B

N-{4-[3-(O-Benzyloxycarboxaldoxime)phenyl]-1-methyl-2-propynyl}-N-hydroxyurea

The diethylacetal resulting from Example 10A (0.26 g, 0.85 mmol) was dissolved in ethanol (8 mL) and water (2 mL). To this stirred solution was added O-benzylhydroxylamine hydrochloride (0.27 g, 1.7 mmol). The mixture was stirred 2 hours at ambient temperature and poured into water. The mixture was extracted thoroughly with ethyl acetate and the combined organic extracts washed with water and brine, dried (MgSO₄) and concentrated in vacuo to give a thick oil that solidified upon standing. Recrystalization from ethyl acetate-hexanes afforded 0.21 g of the title compound. m.p. 146°-148° C. (dec). ¹H NMR (DMSO-d₆, 300 MHz) δ1.36 (d, J=6 Hz, 3H), 5.13 (q, J=6 Hz, 1H), 5.18 (s, 2H), 6.57 (bs, 2H), 7.29-7.47 (m, 7H), 7.57-7.65 (m, 2H), 9.36 (s, 1H). MS (DCI/NH₃) m/e 355 (M+H)⁺.

EXAMPLE 11

N-Hydroxy-N-{3-[(3-phenylcarbonyl)phenyl]-1-methyl-2-propynyl}urea

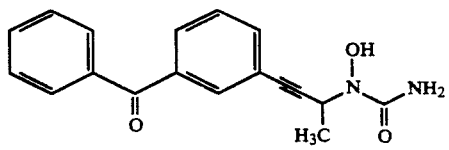

The title compound was prepared following the procedures described in Example 1 using N-methoxy-N-methyl-3-bromobenzamide instead of 4-fluorobenzylbromide and phenylmagnesiumbromide instead of lithiofuran.

EXAMPLE 12

N-{3-[5-(4-Fluorophenylmethyl)-2-thienyl]-1-methyl-2-propynyl}-N-hydroxyurea

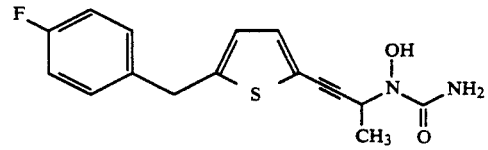

EXAMPLE 12A

2-Bromo-5-(4-fluorophenylmethyl)thiophene

A solution of thiophene (12.6 g, 0.15 mol) in a mixture of anhydrous ether (230 mL) and anhydrous THF (70 mL) was treated dropwise at 0° C. with a 2.5M solution of n-butyllithium in hexane (54.0 mL, 0.134 mol). The mixture was stirred at 0° C. for 1.5 hours and then transferred by cannula into a −78° C. solution of 4-fluorobenzylbromide (23.6 g, 0.125 mol) containing tetrakis(triphenylphosphine) palladium (0) (1.25 g) in anhydrous THF (200 mL). The reaction mixture was stirred at ambient temperature under nitrogen overnight and then quenched with saturated NH₄Cl solution (100 mL) and partitioned between ether and additional NH₄Cl solution. The ether layer was dried over MgSO₄, concentrated in vacuo and the residue subjected to vacuum distillation to give 19.4 g (81%) of 2-(4-fluorophenylmethyl)thiophene. b.p. 74°-83° C. at 0.6-0.7 mm of Hg.

The above thiophene (9.61 g, 50.0 mmol) was brominated using N-bromosuccinimide (8.90 g, 50.0 mmol) in CHCl₃ and CH₃COOH (1:1) to provide 13.3 g (98%) of the title compound.

EXAMPLE 12B

N-{3-[5-(4-Fluorophenylmethyl)-2-thienyl]-1-methyl-2-propynyl}-N-hydroxyurea

Using the procedures described in Example 1C, the compound resulting from Example 12A (13.3 g, 49.0 mmol) was converted to the alcohol intermediate in a yield of 9.16 g (71%).

In a manner analogous to the procedures described in Example 1D, the alcohol intermediate from above was converted to the title compound in 33% yield. m.p. 141°-142° C. (dec.). $^1$H NMR (DMSO-d$_6$, 300 MHz) δ1.32 (d, J=6.0 Hz, 3H), 4.10 (s, 2H), 5.10 (q, J=6.0 Hz, 1H), 6.50 (s, 2H), 6.80 (d, J=3.0 Hz, 1H), 7.05 (d, J=3.0 Hz, 1H), 7.13 (m, 2H), 7.28 (m, 2H), 9.30 (s, 1H). MS (DCI/NH$_3$) m/e 319(M+H)$^+$, 336 (M+H+NH$_3$)$^+$. Analysis calcd for C$_{16}$H$_{15}$FN$_2$O$_2$S: C, 60.36; H, 4.75; N, 8.80. Found: C, 60.53; H, 4.68; N, 8.8.

EXAMPLE 13

(R)-N-{3-[5-(4-Fluorophenylmethyl)-2-thienyl]-1-methyl-2-propynyl}-N-hydroxyurea

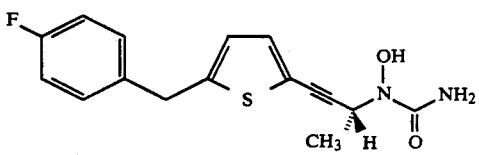

A mixture of 2-(4-fluorophenylmethyl)thiophene, prepared as described in Example 12A, (3.85 g, 20.0 mmol) and N-iodosuccinimide (4.50 g, 20.0 mmol) in 1:1 chloroform-acetic acid (40 mL) was stirred at ambient temperature for 1 hour and then diluted with an equal volume of water. The organic layer was washed with saturated NaHCO$_3$ solution (2×50 mL), 10% aqueous sodium thiosulfate solution (2×50 mL) and once with brine. After drying over MgSO$_4$, the organic layer was concentrated in vacuo to give 6.07 g (95%) of the iodo intermediate as a gold colored oil.

To a solution of the iodo intermediate (5.30 g,16.6 mmol) in anhydrous DMF (5.0 mL) was added diethylamine (56 mL) followed by the (R)-1-methyl-2-propynyl-N-hydroxyurea (2.12 g, 16.6 mmol), triphenylphosphine (84 mg, 0.32 mmol), bis(acetonitrile)palladium(II) chloride (40 mg, 0.16 mmol) and copper(I)iodide (16 mg, 0.08 mmol). The mixture was stirred under nitrogen at ambient temperature for 22 hours followed by concentration in vacuo at 32° C. The residue was subjected to chromatography on silica eluting with 2-7% MeOH in CH$_2$Cl$_2$, crystallization from ethyl acetate-hexane and trituration in CH$_2$Cl$_2$ to afford the title compound as a cream-colored solid 0.94 g (18%). m.p. 135-136° C.(dec). $^1$H NMR (DMSO-d$_6$, 300 MHz) δ1.32 (d, J=6.0 Hz, 3H), 4.11 (s, 2H), 5.10 (q, J=6.0 Hz, 1H), 6.54 (s, 2H), 6.81 (d, J=3.0 Hz, 1H), 7.08 (d, J=3.0 Hz, 1H), 7.10-7.18 (m, 2H), 7.25-7.32 (m, 2H), 9.33 (s, 1H). MS (DCI/NH$_3$) m/e 319 (M+H)$^+$. [α]$^{23}$°= +47.8° (C=1, MeOH). Analysis calcd for C$_{16}$H$_{15}$FN$_2$O$_2$S: C, 60.36; H, 4.75; N, 8.80. Found: C, 60.31; H, 4.79; N, 8.50.

EXAMPLE 14

N-{3-[5-(4-Fluorophenylcarbonyl)-2-thienyl]-1-methyl-2-propynyl}-N-hydroxyurea

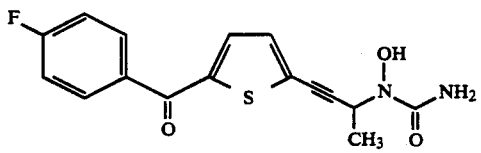

A solution of 2,5-dibromothiophene (19.23 g, 75.5 mmol) in anhydrous THF (400 mL) was treated at −78° C. under nitrogen with a 2.5M solution of n-butyllithium in hexane (30.0 mL, 75.5 mmol). The resulting solution was stirred for 45 minutes at −78° C. and then transferred by cannula into a cold (−78° C.) solution of N-methoxy-N-methyl-4-fluorobenzamide (12.57 g, 68.6 mmol) in anhydrous THF (300 mL) with stirring. After 30 minutes at −78° C., the reaction was quenched by the addition of a saturated solution of NH$_4$Cl (15 mL) and poured into ethanol (350 mL) containing 10% HCl (140 mL). The mixture was partitioned between brine and 1:1 ether and dichloromethane. The organic layer was dried over Na$_2$SO$_4$ and concentrated in vacuo. The residue was crystallized from pentane to give 16.8 g (86%) of the bromoketone intermediate.

In an analogous manner as described in Example 1C, the alcohol intermediate was prepared in 94% yield. In an analogous manner as Example 1D, the title compound was obtained in 63% yield after purification by chromatography on silica eluting with 5-7% CH$_3$OH in CH$_2$Cl$_2$. m.p. 136.5°-138° C. (dec). $^1$H NMR (DMSO-d$_6$, 300 MHz) δ1.38 (d, J=6.0 Hz, 3H), 5.21 (q, J=6.0 Hz, 1H), 6.62 (s, 2H), 7.36-7.45 (m, 3H), 7.65 (d, J=3.0 Hz,1H), 7.90-7.97 (m, 2H), 9.46 (s, 1H). MS (DCI/NH$_3$) m/e 333 (M+H)$^+$. Analysis calcd for C$_{16}$H$_{13}$FN$_2$O$_3$S: C, 57.82; H, 3.94; N, 8.43. Found: C, 57.85; H, 3.84; N, 8.43.

EXAMPLE 15

(R)-N-{3-[5-(3-Chloropyrid-3-ylmethyl)-2-thienyl]-1-methyl-2-propynyl}-N-hydroxyurea

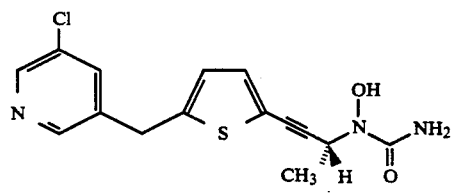

The title compound is prepared using the procedures described in Example 13 substituting 2-(3-chloropyrid-3-ylmethyl)thiophene for 2-(4-fluorophenylmethyl)thiophene.

EXAMPLE 16

(R)-N-{3-[5-(3-Chloropyrid-3-ylmethyl)-2-furyl]-1-methyl-2-propynyl}-N-hydroxyurea

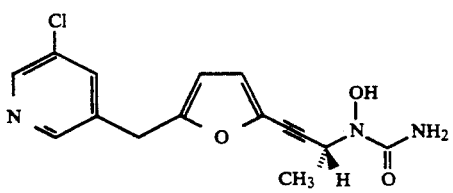

The title compound is prepared using the procedures described in Example 13 substituting 2-(3-chloropyrid-3-ylmethyl)furan for 2-(4-fluorophenylmethyl)thiophene.

EXAMPLE 17

(R)-N-{3-[5-(3-Chloropyrid-3-ylmethyl)-phenyl]-1-methyl-2-propynyl}-N-hydroxyurea

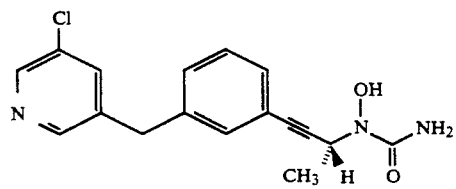

The title compound is prepared using the procedures described in Example 13 substituting (3-chloropyrid-3-ylmethyl)benzene for 2-(4-fluorophenylmethyl)thiophene.

EXAMPLE 18

(R)-N-{3-[5-(4-Chlorophenylmethyl)-2-thienyl]-1-methyl-2-propynyl}-N-hydroxyurea

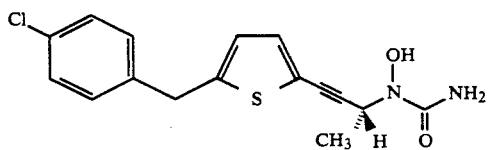

The title compound is prepared using the procedures described in Example 13 substituting 2-(4-chlorophenylmethyl)thiophene for 2-(4-fluorophenylmethyl)thiophene.

EXAMPLE 19

(R)-N-{3-[5-(4-Fluorophenylmethyl)-2-thiazolyl]-1-methyl-2-propynyl}-N-hydroxyurea

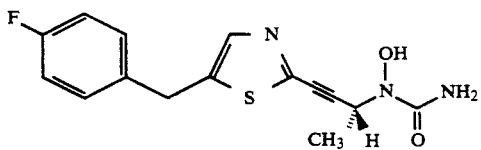

The title compound is prepared using the procedures described in Example 13 substituting 5-(4-fluorophenylmethyl)thiazole for 2-(4-fluorophenylmethyl)thiophene.

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. A compound of the formula:

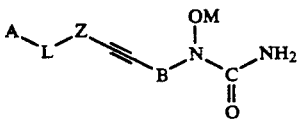

or a pharmaceutically acceptable salt thereof wherein

M is selected from the group consisting of hydrogen, and a pharmaceutically acceptable cation;

B is a straight or branched divalent alkylene group of from one to twelve carbon atoms;

Z is selected from the group consisting of:
  (a) furyl, optionally substituted with alkyl of from one to six carbon atoms, or haloalkyl of from one to six carbon atoms, and
  (b) thienyl, optionally substituted with alkyl of from one to six carbon atoms, or haloalkyl of from one to six carbon atoms; and L is alkylene of from 1–6 carbon atoms;

A is phenyl optionally substituted with
  alkyl of from one to six carbon atoms,
  haloalkyl of from one to six carbon atoms,
  hydroxyalkyl of from one to six carbon atoms,
  alkoxy of from one to twelve carbon atoms,
  alkoxyalkoxyl in which the two alkoxy portions may each independently contain from one to six carbon atoms,
  alkylthio of from one to six carbon atoms,
  hydroxy,
  halogen,
  cyano,
  amino,
  alkylamino of from one to six carbon atoms,
  dialkylamino in which the two alkyl groups may independently contain from one to six carbon atoms,
  alkanoylamino of from two to eight carbon atoms,
  N-alkanoyl-N-alkylamino in which the alkanoyl is of from two to eight carbon atoms and the alkyl group is of from one to six carbon atoms,
  alkylaminocarbonyl of from two to eight carbon atoms,
  dialkylaminocarbonyl in which the two alkyl groups are independently of from one to six carbon atoms,
  carboxyl,
  alkoxycarbonyl of from two to eight carbon atoms,
  phenyl, optionally substituted with alkyl of from one to six carbon atoms, haloalkyl of from one to six carbon atoms, alkoxy of from one to six carbon atoms, hydroxy or halogen,
  phenoxy, optionally substituted with alkyl of from one to six carbon atoms, haloalkyl of from one to six carbon atoms, alkoxy of from one to six carbon atoms, hydroxy or halogen, or
  phenylthio, optionally substituted with alkyl of from one to six carbon atoms, haloalkyl of from one to six carbon atoms, alkoxy of from one to six carbon atoms, hydroxy or halogen 2. A compound or a pharmaceutically acceptable salt thereof as defined by claim 1 wherein Z is furyl, optionally substituted with alkyl of from one to six carbon atoms, or haloalkyl of from one to six carbon atoms; and B, M, L and A are as defined above.

3. A compound or a pharmaceutically acceptable salt thereof as defined by claim 1 wherein Z is thienyl, optionally substituted with alkyl of from one to six carbon atoms, or haloalkyl of from one to six carbon atoms; and B, M, L and A are as defined above.

4. A compound or a pharmaceutically acceptable salt thereof as defined by claim 1 wherein A is phenyl optionally substituted with alkyl of from one to six carbon atoms, haloalkyl of from one to six carbon atoms, hydroxyalkyl of from one to six carbon atoms, alkoxy of from one to twelve carbon atoms, alkoxyalkoxyl in which the two alkoxy portions may each independently contain from one to six carbon atoms, alkylthio of from one to six carbon atoms, hydroxy, halogen, cyano, amino, alkylamino of from one to six carbon atoms, and dialkylamino in which the two alkyl groups may independently contain from one to six carbon atoms; and M, B, Z, and L are as defined above.

5. A compound or a pharmaceutically acceptable salt thereof as defined by claim 1 selected from the group consisting of:

N-{3-(5-(4-fluorophenylmethyl)fur-2-yl)-3-butyn-2-yl}-N-hydroxyurea;

N-{3-(5-(4-fluorophenylmethyl)-2-thienyl)-1-methyl-2-propynyl}-N-hydroxyurea;

(R)-N-{3-(5-(4-fluorophenylmethyl)-2-thienyl)-1-methyl-2-propynyl}-N-hydroxyurea; and (R)-N-{3-(5-(4-chlorophenylmethyl)-2-thienyl)-1-methyl-2-propynyl}-N-hydroxyurea;

6. A compound or a pharmaceutically acceptable salt thereof having the name N-{3-[5-(4-fluorophenylmethyl)-2-thienyl]-1-methyl-2-propynyl}-N-hydroxyurea.

7. A compound or a pharmaceutically acceptable salt thereof having the name (R)-N-{3-[5-(4-fluorophenylmethyl)-2-thienyl]-1-methyl-2-propynyl}-N-hydroxyurea.

8. A compound or a pharmaceutically acceptable salt thereof having the name (S)-N-{3-[5-(4-fluorophenylmethyl)-2-thienyl]-1-methyl-2-propynyl}-N-hydroxyurea.

9. A composition for inhibiting the biosynthesis of leukotrienes comprising a compound as defined by claim 1 in combination with a pharmaceutically acceptable carrier.

10. A method for inhibiting leukotriene biosynthesis in a mammal in need of such treatment, comprising administering to the mammal a therapeutically effective amount of a compound as defined by claim 1.

* * * * *

UNITED STATES PATENT AND TRADEMARK OFFICE
CERTIFICATE OF CORRECTION

PATENT NO. : 5,288,751
DATED : February 22, 1994
INVENTOR(S) : DEE W. BROOKS; ANDREW O. STEWART; ANWER BASHA; PRAMILA BHATIA; JAMES D. RATAJCZYK It is certified that error appears in the above-indentified patent and that said Letters Patent is hereby corrected as shown below:

COLUMNS 13 AND 14, REPLACE

Scheme 1b

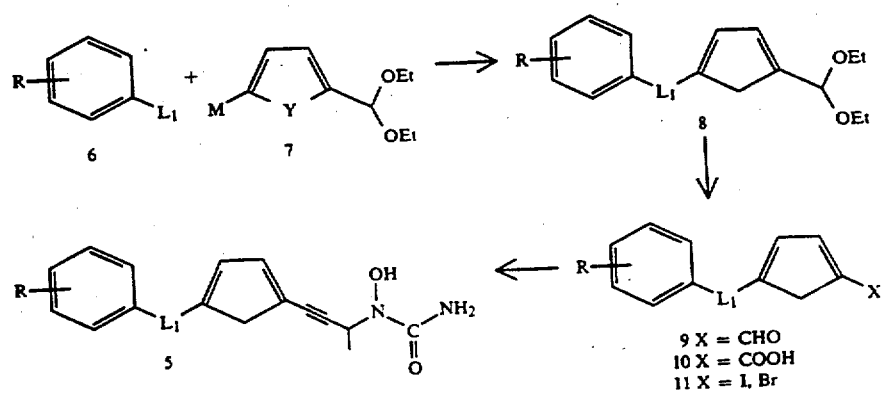

UNITED STATES PATENT AND TRADEMARK OFFICE
CERTIFICATE OF CORRECTION

PATENT NO. : 5,288,751
DATED : February 22, 1994
INVENTOR(S) : DEE W. BROOKS; ANDREW O. STEWART; ANWER BASHA; PRAMILA BHATIA; JAMES D. RATAJCZYK Page 2 of 2

It is certified that error appears in the above-indentified patent and that said Letters Patent is hereby corrected as shown below:

WITH

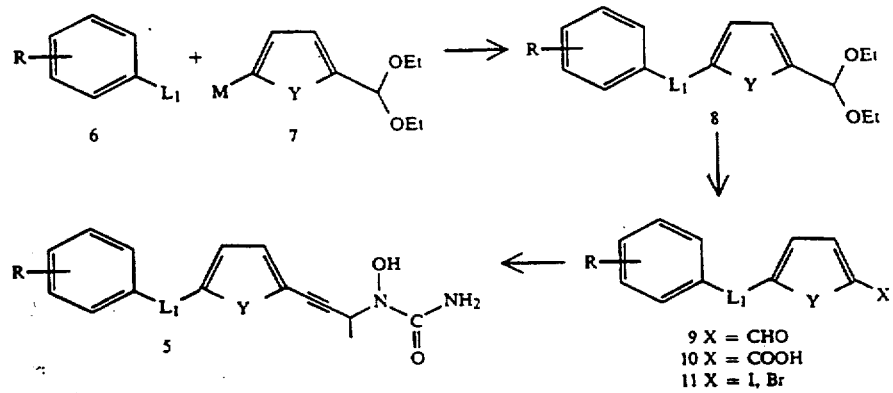

Signed and Sealed this

Thirteenth Day of September, 1994

Attest:

BRUCE LEHMAN

Attesting Officer

Commissioner of Patents and Trademarks